(12) United States Patent
Brandt et al.

(10) Patent No.: US 7,615,216 B2
(45) Date of Patent: Nov. 10, 2009

(54) ANTIBODIES AGAINST CCR5 AND USES THEREOF

(75) Inventors: Michael Brandt, Iffeldorf (DE); Surya Sankuratri, San Jose, CA (US); Ralf Schumacher, Penzberg (DE); Stefan Seeber, Penzberg (DE)

(73) Assignee: Roche Palo Alto LLC, Palo Alto, CA (US)

( * ) Notice: Subject to any disclaimer, the term of this patent is extended or adjusted under 35 U.S.C. 154(b) by 132 days.

(21) Appl. No.: 11/394,439

(22) Filed: Mar. 31, 2006

(65) Prior Publication Data

US 2007/0036796 A1    Feb. 15, 2007

(30) Foreign Application Priority Data

Apr. 1, 2005  (EP)  .................. 05007138

(51) Int. Cl.
| | | |
|---|---|---|
| A61K 39/00 | (2006.01) | |
| A61K 39/395 | (2006.01) | |
| C12N 5/06 | (2006.01) | |
| C12P 21/08 | (2006.01) | |
| C12P 21/06 | (2006.01) | |
| C07H 21/04 | (2006.01) | |

(52) U.S. Cl. .................. 424/133.1; 424/155.1; 435/326; 530/388.8

(58) Field of Classification Search .............. 424/133.1, 424/155.1; 435/326; 530/388.8
See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwashita et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 5,202,238 | A | 4/1993 | Fell, Jr. et al. |
| 5,204,244 | A | 4/1993 | Fell et al. |
| 6,528,625 | B1 | 3/2003 | Wu et al. |
| 6,610,834 | B1 | 8/2003 | Lobo |
| 2001/0000241 | A1 | 4/2001 | Li et al. |
| 2002/0048786 | A1 | 4/2002 | Rosen et al. |
| 2002/0061834 | A1 | 5/2002 | Rosen et al. |
| 2002/0106374 | A1 | 8/2002 | Olson et al. |
| 2002/0146415 | A1 | 10/2002 | Olson et al. |
| 2002/0147147 | A1 | 10/2002 | Molling et al. |
| 2003/0003440 | A1 | 1/2003 | Lopalco |
| 2003/0044411 | A1 | 3/2003 | Olson et al. |
| 2003/0049251 | A1 | 3/2003 | Barbas et al. |
| 2003/0099645 | A1 | 5/2003 | Lobo |
| 2003/0100058 | A1 | 5/2003 | Roschke et al. |
| 2003/0152913 | A1 | 8/2003 | Hua et al. |
| 2003/0165988 | A1 | 9/2003 | Hua et al. |
| 2003/0166024 | A1 | 9/2003 | Rosen et al. |
| 2003/0166870 | A1 | 9/2003 | Wu et al. |
| 2003/0195348 | A1 | 10/2003 | Combadiere et al. |
| 2003/0228306 | A1 | 12/2003 | Olson et al. |
| 2004/0043033 | A1 | 3/2004 | Green |

FOREIGN PATENT DOCUMENTS

| | | |
|---|---|---|
| EP | 0 307 434 B1 | 9/1993 |
| EP | 1 207 202 A1 | 5/2002 |
| EP | 1 161 456 B1 | 12/2004 |
| WO | WO 87/05330 A1 | 9/1987 |
| WO | WO 88/07089 | 9/1988 |
| WO | WO 98/52976 A1 | 11/1998 |
| WO | WO 00/34317 A2 | 6/2000 |
| WO | WO 00/35409 A2 | 6/2000 |
| WO | WO 01/42308 A2 | 6/2001 |
| WO | WO 01/43779 A2 | 6/2001 |
| WO | WO 01/58915 A2 | 8/2001 |
| WO | WO 01/58916 A2 | 8/2001 |
| WO | WO 02/22077 A2 | 3/2002 |
| WO | WO 02/083172 A1 | 10/2002 |
| WO | WO 03/033666 A2 | 4/2003 |
| WO | WO 03/066830 A2 | 8/2003 |
| WO | WO 03/072766 A1 | 9/2003 |

OTHER PUBLICATIONS

Fundamental Immunology 242 (William E. Paul, M.D. ed., 3d ed. 1993).*
Rudikoff et al (Proc Natl Acad Sci,USA 1982 vol. 79 p. 1979).*
Casset et al. ((2003) BBRC 307, 198-205).*
Holm et al (Molec. Immunol. (2007) 44, 1075-1084).*
MacCallum et al. (J. Mol. Biol. (1996) 262, 732-745).*
Jang et al. (Molec. Immunol. 35:1207-1217 (1998)).*
Vincenti, Am. J. Transpl. 2:898-903 (2002).*
Shaheen et al., Curr. Opin. Infect. Dis. 17:7-16 (2004).*
Choudry et al., Expert Opin. Biol. Ther. 6:523-531 (2006).*
Adachi, A., et al., "Production of Acquired Immunodeficiency Syndrome-Associated Retrovirus in Human and Nonhuman Cells Transfected with an Infectious Molecular Clone," *Journal of Virology* 59 (1986) 284-291.
Angal, S., et al., "A Single Amino Acid Substitution Abolishes the Heterogeneity of Chimeric Mouse/Human IgG4 Antibody," *Molecular Immunology*. 30 (1993) 105-108.
Aplin, J.D., et al., "Preparation, Properties, and Applications of Carbohydrates Conjugates of Proteins and Lipids," *CRC Crit. Rev. Biochem.* 4 (1981) 259-306.
Barnes, L.M., et al., "Characterization of the Stability of Recombinant Protein Production in the GS-NS0 Expression System," *Biotech. Bioeng.* 73 (2001) 261-270.

(Continued)

*Primary Examiner*—Lynn A. Bristol
(74) *Attorney, Agent, or Firm*—Grant D. Green

(57) ABSTRACT

Antibodies that specifically bind to CCR5 are useful for treating immunosuppressive disease.

7 Claims, No Drawings

OTHER PUBLICATIONS

Barnes, L.M., et al., "Advances in Animal Cell Recombinant Protein Production: GS-NS0 Expression System," *Cytotechnology* 32 (2000) 109-123.

Brunhouse, R., et al., Isotypes of IgG: Comparison of the Primary Structures of Three Pairs of Isotypes which Differ in their Ability to Activate complement, *Molecular Immunology.* 16 (1979) 907-917.

Burton D.R., et al., "The C1q Receptor site on immunoglobulin G," *Nature* 288 (1980) 338-344.

Carter, P., et al., "Humanization of an Anti-p185$^{HER2}$ Anibody Human Cancer Theapy," *Proc. Natl. Acad. Sci,* 89 (1992) 4285-4289.

Dean, M., et al., "Genetic Restriction of HIV-1 Infection and Progression to AIDS by a Deletion Allele of the CKR5 Structural Gene," *Science* 273 (1996) 1856-1852.

Durocher, Y., et al., "High-level and high-throughput Recombinant Protein Production by Transient Transfection of Suspension-growing human 293-EBNA1 Cells," *Nucleic Acids Research* 30 (2002) E9.

Edelman, G.M., et al., "The Covalent Structure of Entire_G Immunoglobin Molecule." *Natl. Acad. Sci. USA* 63 (1969) 78-85.

Edge, A.S., et al., "Deglycosylation of Glycoproteins by Trifluoromethanesulfonic Acid," *Analytical Biochemistry* 118 (1981) 131-137.

Geisse, S. et al., "Eukaryotic Expression Systems: A Comparison," *Protein Expression and Purification* 8 (1996) 271-282.

Herareh, M., et al., "Effector Function Activities of a Panel of Mutants of a Broadly Neutralizing Antibody against Human Immunodeficiency Virus Type 1," *J of Virology* 75 (2001) 12161-12168.

Idusogie E.E., et al., "Mapping of the C1q Binding Site of Rituxan, a Chimeric Antibody with a Human IgG1 Fc," *J. Immunology* 164 (2000) 4178-4184.

Johnson, G., et al., "Kabat Database and its applications: 30 years after the first variability plot," *Nucleic Acids Research* 28 (2000) 214-218.

Kaufman, R.J., "Overview of Vector Design for Mammalian Gene Expression," *Molecular Biotechnology* 16 (2000) 151-160.

Lee, B. et al., "Epitope Mapping of CCR5 Reveals Multiple Conformational States and Distinct but Overlapping Structures Involved in Chemokine and Coreceptor Function," *J. of Biological Chem.* 274 (1999) 9617-9626.

Lukas, T.J., et al., "Inhibition of C1-Mediated Immune Hemolysis by Monomeric and Dimeric Peptides from the Second Constant Domain of Human Immunoglobulin G$^1$," *Journal of Immunology* 127 (1981) 2555-2560.

Lund, J., et al., "Oligosaccharide-protein Interations in IgG can Moldulate Recognition by Fcγ Receptors," *FASEB* 9 (1995) 115-119.

Makrides, S.C., "Components of Vectors for Gene Transfer and Expression in Mammalian Cells," *Protein Expression and Purification* 17 (1999) 183-202.

Morgan, A., et al., "The N-terminal end of the $C_H2$ Domain of Chimeric Human IgG1 Anti-HLA-DR is necessary for C1q, FcγRI and FcγRIII Binding," *Immunology* 86 (1996) 319-324.

Morrison, S.L., et al., "Chimeric Human Antibody Molecules: Mouse Antigen-binding Domains with Human Constant Region Domains," *Proc. Natational. Acad. Science USA* 81 (1984) 6851-6855.

Neuberger, M.S. et al., "A Hapten-specific Chimaeric IgE Antibody with Human Physiological Effector Function," *Nature* 314 (1985) 268-270.

Norderhaug, L., et al., "Versatile Vectors for Transient and Stable Expression of Recombinant Antibody Molecules in Mammalian Cells," *Journal of Immunological Methods.* 204 (1997) 77-87.

O'Brien, W.A., et al., HIV-1 tropism for Mononucleart Phagocytes can be determined by Regions of gp120 outside the CD-4 binding domain.

Olson, W.C., et al., "Differential Inhibition of Human Immunodeficiency Virus Type 1 Fusion, gp120 Binding, and CC-Chemoking Activity by Monoclonal Antibodies to CCR5," *Journal of Virology* 73 (1999) 4145-4155.

Oppermann, M., "Chemokine Receptor CCR5: Insights into Structure, Function and Regulation," *Cellular Signalling* 10 (2004) 1201-1210.

Orlandi, R., et al., "Cloning Immunoglobulin Variable Domains for Expression by the Polymerase Chain Reaction," Proc. National. Academic Science USA 86 (1989) 3833-3837.

Queen, C., et al., "A Humanized Antibody that binds to the Interleukin 2 Receptor," *Proc. National Academic Science USA* 86 (1989) 10029-10033.

Riechmann, L., et al., "Reshaping Human Anti-bodies for Therapy," *Nature* 332 (1988) 323-327

Schlaeger, E.J., et al., "Transient Gene Expression in Mammalian Cells grown in Serum-free Suspension Culture," *Cytotechnology* 30 (1999) 71-83.

Schlaeger, E.J., et al., "The Protein Hydrolysate, Primatone RL, is a cost effective Multiple Growth Promoter of Mammalian Cell Culture in Serum-containing and Serum-free Media and Displays Anti-apoptosis Properties," *Journal of Immunology Methods* 194 (1996) 191-199.

Schwarz, M.K., et al., "New Therapeutics that Modulate Chemokine Networks," *Nature Reviews Drug Discovery* 1 (2002) 347-358.

Shields, R.L., et al., "High Resolution mapping of the Binding Site on Human IgG1 for FcγRI, FcγRII, FcγRIII and FcRn and Design of IgG1 Variants with Improved Binding to the FcγR," *J. Biological Chemistry* 276 (2001) 6591-6604.

Sojar, R.L., et al., "A Chemical Method for the Deglycosylation of Proteins," *Arch. Biochem. Biophys.* 259 (1987) 52-57.

Spenlehauser, C. et al "A Luciferase-Reporter Gene-Expressing T-Cell Line Facilitates Neutralization and Drug-Sensitivity Assays that use Either R5 or X4 Strains of Human Immunodeficiency Virus Type 1," *Virology* 280 (2001) 292-300.

Thommesen, J.E. et al., "Lysine 322 in the human IgG3 $C_H2$ Domain is Crucial for Antibody Dependent Complement Activation," *Molecular Immunology* 37 (2000) 995-1004.

Thotakura, N.R., et al., "Enzymatic Deglycosylation of Glycoproteins," *Methods in Enzymology* 138 (1987) 350-359.

Trkola, A., et al., "A Cell Line-Based Neutralization Assay for Primary Human Immunodeficiency Virus Type 1 Isolates that use either the CCR5 or the CXCR4 Coreceptor," *Journal of Virology* 73 (1999) 8966-8974.

Tsimanis, T., et al., "Soluble Chemokine CCR5 Receptor is Present in Human Plasma," *Immunology Letters* 96 (2005) 55-61.

Werner, R.G., et al., "Appropriate Mammalian Expression Systems for Biopharmaceutical," *Drug Res* 48 (1998) 870-880.

\* cited by examiner

SEQUENCE LISTING

```
<160> NUMBER OF SEQ ID NOS: 28

<210> SEQ ID NO 1
<211> LENGTH: 119
<212> TYPE: PRT
<213> ORGANISM: mouse

<400> SEQUENCE: 1

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Val
        35                  40                  45

Ala Ser Ile Ser Thr Gly Asp Asn Thr Tyr Tyr Thr Asp Ser Val Arg
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Phe Cys Thr
                85                  90                  95

Arg Gly Arg Gly Asp Arg Gly Asp Leu Phe Gly Tyr Trp Gly Gln Gly
            100                 105                 110

Thr Leu Val Thr Val Ser Ser
        115
```

-continued

```
<210> SEQ ID NO 2
<211> LENGTH: 114
<212> TYPE: PRT
<213> ORGANISM: mouse

<400> SEQUENCE: 2
```

Asp Ile Val Met Ser Gln Ser Pro Ser Ser Leu Ala Val Ser Val Gly
1               5                   10                  15

Glu Lys Val Thr Met Ser Cys Lys Ser Gln Ser Leu Leu Tyr Arg
            20                  25                  30

Gly Asn Gln Met Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Glu Phe Thr Leu Thr
65                  70                  75                  80

Ile Ser Ser Val Lys Ala Glu Asp Leu Thr Val Tyr Tyr Cys Gln Gln
                85                  90                  95

Tyr Tyr Thr Tyr Pro Arg Thr Phe Gly Gly Gly Thr Lys Leu Glu Ile
            100                 105                 110

Lys Arg

```
<210> SEQ ID NO 3
<211> LENGTH: 117
<212> TYPE: PRT
<213> ORGANISM: mouse

<400> SEQUENCE: 3
```

Gln Val Gln Leu Lys Gln Ser Gly Pro Gly Leu Val Arg Pro Ser Gln
1               5                   10                  15

Ser Leu Ser Ile Thr Cys Thr Val Ser Gly Phe Pro Leu Gly Val Phe
            20                  25                  30

Gly Val His Trp Val Arg Gln Ser Pro Gly Lys Gly Leu Glu Trp Leu
        35                  40                  45

Gly Val Ile Trp Lys Gly Gly Asn Thr Asp Tyr Asn Ala Ala Phe Met
    50                  55                  60

Ser Arg Leu Arg Ile Ser Lys Asp Asn Ser Lys Ser Gln Val Phe Phe
65                  70                  75                  80

Arg Met Asn Ser Leu Gln Thr Asp Asp Thr Ala Ile Tyr Tyr Cys Ala
                85                  90                  95

Lys Val Asn Leu Ala Asp Ala Met Asp Tyr Trp Gly Gln Gly Thr Ser
            100                 105                 110

Val Ile Val Ser Ser
        115

```
<210> SEQ ID NO 4
<211> LENGTH: 108
<212> TYPE: PRT
<213> ORGANISM: mouse

<400> SEQUENCE: 4
```

Asp Ile Gln Met Thr Gln Ser Pro Ala Ser Leu Ser Ala Ser Val Gly
1               5                   10                  15

Glu Thr Val Thr Ile Thr Cys Arg Ser Ser Gly Asn Ile His Gly Tyr
            20                  25                  30

Leu Ala Trp Phe Gln Gln Lys Gln Gly Lys Ser Pro Gln Leu Leu Val
        35                  40                  45

```
Tyr Asn Thr Lys Ala Leu Ala Glu Gly Val Pro Ser Arg Phe Ser Gly
         50                  55                  60

Ser Gly Ser Gly Thr Gln Phe Ser Leu Lys Ile Asn Asn Leu Gln Pro
 65                  70                  75                  80

Glu Asp Phe Gly Ile Tyr Tyr Cys Gln His His Tyr Asp Leu Pro Arg
                 85                  90                  95

Thr Phe Gly Gly Gly Thr Lys Leu Glu Ile Lys Arg
                100                 105
```

<210> SEQ ID NO 5
<211> LENGTH: 117
<212> TYPE: PRT
<213> ORGANISM: mouse

<400> SEQUENCE: 5

```
Gln Val Gln Leu Lys Gln Ser Gly Pro Gly Leu Val Arg Pro Ser Gln
 1               5                  10                  15

Ser Leu Ser Ile Thr Cys Thr Val Ser Gly Phe Pro Leu Gly Ile Phe
                 20                  25                  30

Gly Val His Trp Val Arg Gln Ser Pro Gly Lys Gly Leu Glu Trp Leu
             35                  40                  45

Gly Val Ile Trp Lys Gly Gly Asn Thr Asp Tyr Asn Ala Ala Phe Met
         50                  55                  60

Ser Arg Leu Arg Ile Thr Lys Asp Asn Ser Lys Ser Gln Val Phe Phe
 65                  70                  75                  80

Arg Met Asn Ser Leu Gln Thr Asp Thr Ala Ile Tyr Tyr Cys Ala
                 85                  90                  95

Lys Val Asn Leu Ala Asp Ala Met Asp Tyr Trp Gly Gln Gly Thr Ser
                100                 105                 110

Val Ile Val Ser Ser
        115
```

<210> SEQ ID NO 6
<211> LENGTH: 108
<212> TYPE: PRT
<213> ORGANISM: mouse

<400> SEQUENCE: 6

```
Asp Ile Gln Met Thr Gln Ser Pro Ala Ser Leu Ser Ala Ser Val Gly
 1               5                  10                  15

Glu Thr Val Thr Ile Thr Cys Arg Ala Ser Gly Asn Ile His Gly Tyr
                 20                  25                  30

Leu Ala Trp Phe Gln Gln Lys Gln Gly Lys Ser Pro Gln Leu Leu Val
             35                  40                  45

Tyr Asn Thr Lys Thr Leu Ala Glu Gly Val Pro Ser Arg Phe Ser Gly
         50                  55                  60

Ser Gly Ser Gly Thr Gln Phe Ser Leu Lys Ile Asn Ser Leu Gln Pro
 65                  70                  75                  80

Glu Asp Phe Gly Asn Tyr Tyr Cys Gln His His Tyr Asp Leu Pro Arg
                 85                  90                  95

Thr Phe Gly Gly Gly Thr Lys Leu Glu Ile Lys Arg
                100                 105
```

<210> SEQ ID NO 7
<211> LENGTH: 117
<212> TYPE: PRT
<213> ORGANISM: mouse

<400> SEQUENCE: 7

Gln Val Gln Leu Lys Gln Ser Gly Pro Gly Leu Val Arg Pro Ser Gln
1               5                   10                  15

Ser Leu Ser Ile Thr Cys Thr Val Ser Gly Phe Pro Leu Gly Thr Phe
            20                  25                  30

Gly Val His Trp Val Arg Gln Ser Pro Gly Lys Gly Leu Glu Trp Leu
        35                  40                  45

Gly Val Ile Trp Arg Gly Gly Asn Thr Asp Tyr Asn Ala Ala Phe Met
    50                  55                  60

Ser Arg Leu Arg Ile Thr Lys Asp Asn Ser Lys Ser Gln Val Phe Phe
65                  70                  75                  80

Arg Met Asn Ser Leu Gln Thr Asp Asp Thr Ala Ile Tyr Tyr Cys Ala
                85                  90                  95

Lys Val Asn Leu Ala Asp Ala Met Asp Tyr Trp Gly Gln Gly Thr Ser
            100                 105                 110

Val Ile Val Ser Ser
            115

<210> SEQ ID NO 8
<211> LENGTH: 108
<212> TYPE: PRT
<213> ORGANISM: mouse

<400> SEQUENCE: 8

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Gly Tyr
            20                  25                  30

Leu Ala Trp Phe Gln Gln Lys Gln Gly Lys Ser Pro Gln Leu Leu Val
        35                  40                  45

Tyr Asn Thr Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Asn Tyr Tyr Cys Gln His His Tyr Asp Leu Pro Arg
                85                  90                  95

Thr Phe Gly Gly Gly Thr Lys Leu Glu Ile Lys Arg
            100                 105

<210> SEQ ID NO 9
<211> LENGTH: 5
<212> TYPE: PRT
<213> ORGANISM: mouse

<400> SEQUENCE: 9

Thr Tyr Ala Met Ser
1               5

<210> SEQ ID NO 10
<211> LENGTH: 5
<212> TYPE: PRT
<213> ORGANISM: mouse

<400> SEQUENCE: 10

Val Phe Gly Val His
1               5

<210> SEQ ID NO 11

```
<211> LENGTH: 5
<212> TYPE: PRT
<213> ORGANISM: mouse

<400> SEQUENCE: 11

Ile Phe Gly Val His
1               5

<210> SEQ ID NO 12
<211> LENGTH: 5
<212> TYPE: PRT
<213> ORGANISM: mouse

<400> SEQUENCE: 12

Thr Phe Gly Val His
1               5

<210> SEQ ID NO 13
<211> LENGTH: 16
<212> TYPE: PRT
<213> ORGANISM: mouse

<400> SEQUENCE: 13

Ser Ile Ser Thr Gly Asp Asn Thr Tyr Tyr Thr Asp Ser Val Arg Gly
1               5                   10                  15

<210> SEQ ID NO 14
<211> LENGTH: 16
<212> TYPE: PRT
<213> ORGANISM: mouse

<400> SEQUENCE: 14

Val Ile Trp Lys Gly Gly Asn Thr Asp Tyr Asn Ala Ala Phe Met Ser
1               5                   10                  15

<210> SEQ ID NO 15
<211> LENGTH: 16
<212> TYPE: PRT
<213> ORGANISM: mouse

<400> SEQUENCE: 15

Val Ile Trp Arg Gly Gly Asn Thr Asp Tyr Asn Ala Ala Phe Met Ser
1               5                   10                  15

<210> SEQ ID NO 16
<211> LENGTH: 11
<212> TYPE: PRT
<213> ORGANISM: mouse

<400> SEQUENCE: 16

Gly Arg Gly Asp Arg Gly Asp Leu Phe Gly Tyr
1               5                   10

<210> SEQ ID NO 17
<211> LENGTH: 9
<212> TYPE: PRT
<213> ORGANISM: mouse

<400> SEQUENCE: 17

Val Asn Leu Ala Asp Ala Met Asp Tyr
1               5

<210> SEQ ID NO 18
<211> LENGTH: 17
<212> TYPE: PRT
```

```
<213> ORGANISM: mouse

<400> SEQUENCE: 18

Lys Ser Ser Gln Ser Leu Leu Tyr Arg Gly Asn Gln Met Asn Tyr Leu
1               5                   10                  15
Ala

<210> SEQ ID NO 19
<211> LENGTH: 11
<212> TYPE: PRT
<213> ORGANISM: mouse

<400> SEQUENCE: 19

Arg Ser Ser Gly Asn Ile His Gly Tyr Leu Ala
1               5                   10

<210> SEQ ID NO 20
<211> LENGTH: 11
<212> TYPE: PRT
<213> ORGANISM: mouse

<400> SEQUENCE: 20

Arg Ala Ser Gly Asn Ile His Gly Tyr Leu Ala
1               5                   10

<210> SEQ ID NO 21
<211> LENGTH: 7
<212> TYPE: PRT
<213> ORGANISM: mouse

<400> SEQUENCE: 21

Trp Ala Ser Thr Arg Glu Ser
1               5

<210> SEQ ID NO 22
<211> LENGTH: 7
<212> TYPE: PRT
<213> ORGANISM: mouse

<400> SEQUENCE: 22

Asn Thr Lys Ala Leu Ala Glu
1               5

<210> SEQ ID NO 23
<211> LENGTH: 7
<212> TYPE: PRT
<213> ORGANISM: mouse

<400> SEQUENCE: 23

Asn Thr Lys Thr Leu Ala Glu
1               5

<210> SEQ ID NO 24
<211> LENGTH: 9
<212> TYPE: PRT
<213> ORGANISM: mouse

<400> SEQUENCE: 24

Gln Gln Tyr Tyr Thr Tyr Pro Arg Thr
1               5

<210> SEQ ID NO 25
<211> LENGTH: 9
<212> TYPE: PRT
<213> ORGANISM: mouse
```

<400> SEQUENCE: 25

Gln His His Tyr Asp Leu Pro Arg Thr
1               5

<210> SEQ ID NO 26
<211> LENGTH: 330
<212> TYPE: PRT
<213> ORGANISM: homo sapiens

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27

<211> LENGTH: 282
<212> TYPE: PRT
<213> ORGANISM: Homo sapiens

<400> SEQUENCE: 27

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly
        275                 280
```

<210> SEQ ID NO 28
<211> LENGTH: 107
<212> TYPE: PRT
<213> ORGANISM: Homo sapiens

<400> SEQUENCE: 28

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

```
Thr Tyr Ser Leu Ser Ser Thr Leu Thr Leu Ser Lys Ala Asp Tyr Glu
65              70              75              80

Lys His Lys Val Tyr Ala Cys Glu Val Thr His Gln Gly Leu Ser Ser
                85              90              95

Pro Val Thr Lys Ser Phe Asn Arg Gly Glu Cys
            100             105
```

ANTIBODIES AGAINST CCR5 AND USES THEREOF

RELATED APPLICATIONS

This application claims priority under 35 USC §119 from EP05 007138.0, filed Apr. 1, 2005, incorporated herein by reference in full.

FIELD OF THE INVENTION

The present invention relates to antibodies against CCR5, methods for their production, pharmaceutical compositions containing said antibodies, and uses thereof.

BACKGROUND OF THE INVENTION

Over the past few years a growing understanding of the specific mechanisms that HIV-1 uses to enter target cells has emerged. This facilitated efforts to develop drugs that attack discrete steps in this process. The first drug to target entry has recently been approved for clinical use (enfuvirtide, T20; A. Lazzarin et al., *N. Engl J. Med.* (2003) 348:2186-95). Enfuvirtide is a peptide drug that blocks fusion at a stage subsequent to chemokine receptor binding.

HIV-1 infection is initiated by interactions between the viral envelope glycoprotein (Env) and a cellular receptor complex comprised of CD4 plus a chemokine receptor (T. C. Pierson and R. W. Doms, *Immuno. Lett.* (2003) 85:113-18; and J. M. Kilby and J. J. Eron, *N. Engl. J. Med.* (2003) 348:2228-38). Env has two subunits: the surface glycoprotein gp120 which interacts with the cellular CD4-receptors and which is non-covalently associated with the virus transmembrane subunit gp41. Gp41 anchors gp120 to the viral membrane, and is also responsible for fusion. Binding of gp120 to CD4 on cells triggers a conformational change that exposes or creates a binding site that enables gp120 to interact with a cell surface chemokine receptor, the "co-receptor". Chemokine receptors are seven transmembrane G-protein coupled receptors (7 TM GPCRs) that normally transmit signals in response to chemokines, small cytokines with chemotactic, inflammatory and other functions.

A large proportion of drugs in clinical use are directed at other 7TM GPCRs, and so targeting these molecules to block viral entry is an extension of the most successful type of drug development programs of the past. HIV-1 isolates require CD4 and a coreceptor to enter and infect cells. The CC chemokine receptor CCR5 is a co-receptor for macrophage-tropic (R5) strains and plays a crucial role in the sexual transmission of HIV-1 (E. A. Berger, *AIDS*(1997) 11(Suppl. A):S3-S16; P. D. Bieniasz and B. R. Cullen, *Frontiers in Bioscience* (1998) 3:44-58; D. R. Littman, *Cell* (1998) 93:677-680).

CCR5 is used by most HIV-1 primary isolates and is critical for the establishment and maintenance of infection. In addition CCR5 function is dispensable for human health. A mutant CCR5 allele, "CCR5Δ32", encodes a truncated, non-functional protein (M. Samson et al., *Nature* (1996) 382:722-25; M. Dean et al., *Science* (1996) 273:1856-62). Individuals homozygous for the mutation lack CCR5 expression and are strongly protected from HIV-1 infection. They demonstrate no overt phenotype consequence and are highly resistant to M tropic HIV infection, whereas heterozygote individuals present delayed disease progression (M. K. Schwarz and T. N. Wells, *Nat. Rev. Drug Discov.* (2002) 1:347-58). The lack of CCR5 is without apparent adverse consequences, probably because CCR5 is part of a highly redundant chemokine network as receptor for the α chemokines MIP-1α, MIP-1β and RANTES, which share many overlapping functions, and most of which have alternative receptors (D. Rossi and A. Zlotnik, *Annu. Rev. Immunol.* (2000) 18:217-243). The identification of CCR5 as an HIV-1 co-receptor was based on the ability of its ligands, MIP-1α, MIP-1β and RANTES to block infection by R5 but not R5X4 or X4 isolates (F. Cocchi et al., *Science* (1995) 270:1811-15).

CCR5 is also a receptor of the "cluster" chemokines that are produced primarily during inflammatory responses and control the recruitment of neutrophils (CXC chemokines) and macrophages and subsets of T cells. (T helper Th1 and Th2 cells). Th1 responses are typically those involving cell-mediated immunity effective against viruses and tumors, for example, whereas Th2 responses are believed to be pivotal in allergies. Therefore, inhibitors of these chemokine receptors may be useful as immunomodulators. For Th1 responses, overactive responses are dampened, for example, in autoimmunity including rheumatoid arthritis or, for Th2 responses, to lessen asthma attacks or allergic responses including atopic dermatitis. (see e.g. D. Schols, *Curr. Top. Med. Chem.* (2004) 4:883-893; A. Mueller and P. G. Strange, *Int. J. Biochem. Cell Biol.* (2004) 36:35-38; W. M. Kazmierski et al., *Curr. Drug Targets Infect. Disord.* (2002) 2:265-278; T. Lehner, *Trends Immunol.* (2002) 23:347-51).

Antibodies against CCR5 are e.g. PRO 140 (W. C. Olson et al., *J. Virol.* (1999) 73:4145-55) and 2D7 (M. Samson et al., *J. Biol. Chem* (1997) 272:24934-41). Additonal antibodies are mentioned in US2004-0043033, U.S. Pat. No. 6,610,834, US2003-0228306, US2003-0195348, US2003-0166870, US2003-0166024, US2003-0165988, US2003-0152913, US2003-0100058, US2003-0099645, US2003-0049251, US2003-0044411, US2003-0003440, U.S. Pat. No. 6,528,625, US2002-0147147, US2002-0146415, US2002-0106374, US2002-0061834, US2002-0048786, US2001-0000241, EP1322332, EP1263791, EP1207202, EP1161456, EP1144006, WO2003/072766, WO2003/066830, WO2003/033666, WO02/083172, WO02/22077, WO01/58916, WO01/58915, WO01/43779, and WO01/42308.

SUMMARY OF THE INVENTION

An object of the invention is to provide novel antibodies against CCR5 which can be used as a therapeutic agent for AIDS.

The invention comprises an antibody binding to CCR5 characterized in that the variable heavy chain amino acid sequence CDR3 of said antibody is selected from the group consisting of the heavy chain CDR3 sequences SEQ ID NO: 16 or 17.

The invention preferably provides an antibody binding to CCR5, comprising a variable heavy chain and a variable light chain, characterized in that the variable heavy chain comprises CDR sequences CDR1, CDR2 and CDR3 and CDR1 being selected from the group consisting of SEQ ID NOs: 9, 10, 11, 12, CDR2 being selected from the group consisting of SEQ ID NOs: 13, 14, 15, CDR3 being selected from the group consisting of SEQ ID NOs: 16,17, wherein said CDRs are selected independently of each other.

The antibody according to the invention is preferably characterized in that the variable light chain comprises CDR sequences CDR1, CDR2 and CDR3, and CDR1 is selected from SEQ ID NOs: 18, 19, 20, CDR2 is selected from SEQ ID NOs: 21, 22, 23 and CDR3 is selected from SEQ ID NOs: 24 or 25 wherein said CDRs are selected independently of each other.

The antibody is preferably characterized in containing as heavy chain CDRs the CDRs of SEQ ID NO: 1 and as light chain CDRs the CDRs of SEQ ID NO: 2, as heavy chain CDRs the CDRs of SEQ ID NO: 3 and as light chain CDRs the CDRs of SEQ ID NO: 4, as heavy chain CDRs the CDRs of SEQ ID NO: 5 and as light chain CDRs the CDRs of SEQ ID NO: 6, as heavy chain CDRs the CDRs of SEQ ID NO: 7 and as light chain CDRs the CDRs of SEQ ID NO: 8.

The CDR sequences can be determined according to the standard definition of Kabat et al., Sequences of Proteins of Immunological Interest, 5th ed., Public Health Service, National Institutes of Health, Bethesda, Md. (1991). CDRs of SEQ ID NO: 1-8 are shown in SEQ ID NO: 9-25.

CDRs on each chain are separated by framework amino acids.

The antibody according to the invention is preferably characterized in that said antibody binds CCR5 and comprises a variable heavy and light region independently selected from the group consisting of a) the heavy chain ($V_H$) variable domain defined by amino acid sequence SEQ ID NO:1 and the light chain ($V_H$) variable domain defined by SEQ ID NO:2;
b) the heavy chain variable domain defined by amino acid sequence SEQ ID NO:3 and the light chain variable domain defined by SEQ ID NO:4;
c) the heavy chain variable domain defined by amino acid sequence SEQ ID NO:5 and the light chain variable domain defined by SEQ ID NO:6;
d) the heavy chain variable domain defined by amino acid sequence SEQ ID NO:7 and the light chain variable domain defined by SEQ ID NO:8;

or a CCR5-binding fragment thereof.

The antibody according to the invention is preferably characterized in that the heavy chain variable region comprises an amino acid sequence independently selected from the group consisting of SEQ ID NO: 1, 3, 5 and 7.

The antibody according to the invention is preferably characterized in that the light chain variable region comprises an amino acid sequence independently selected from the group consisting of SEQ ID NO: 2, 4, 6, and 8.

The antibody according to the invention is preferably characterized in that the constant chains are of human origin. Such constant chains are well known in the state of the art and e.g. described by Kabat (see e.g. G. Johnson and T. T. Wu, *Nuc Acids Res.* (2000) 28:214-18). For example, a useful human heavy chain constant region comprises an amino acid sequence independently selected from the group consisting of SEQ ID NO: 26 and 27. For example, a useful human light chain constant region comprises an amino acid sequence of a kappa-light chain constant region of SEQ ID NO: 28. It is further preferred that the antibody is of mouse origin and comprises the antibody variable sequence frame of a mouse antibody according to Kabat (see e.g. G. Johnson and T. T. Wu, supra).

The antibodies inhibit one or more functions of human CCR5, such as ligand binding to CCR5, signaling activity (e.g., activation of a mammalian G protein, induction of a rapid and transient increase in the concentration of cytosolic free $Ca^{2+}$ and/or stimulation of a cellular response (e.g., stimulation of chemotaxis, exocytosis or inflammatory mediator release by leukocytes, integrin activation)). The antibodies inhibit binding of RANTES, MIP-1α, MIP-1β and/or HIV to human CCR5 and inhibit functions mediated by human CCR5, like leukocyte trafficking, HIV entry into a cell, T cell activation, inflammatory mediator release and/or leukocyte degranulation.

The antibody according to the invention specifically binds to human CCR5 and inhibits the HIV fusion with a target cell in an assay comprising contacting the virus, in the presence of said target cell, with the antibody in a concentration effective to inhibit membrane fusion between the virus and said cell with an $IC_{50}$ value of 4.0 µg/ml or lower.

The antibody according to the invention specifically binds to CCR5 and inhibits membrane fusion between a first cell co-expressing CCR5 and CD4 polypeptides and a second cell expressing an HIV env protein with an $IC_{50}$ value of 1.5 µg/ml or lower, preferably 0.3 µg/ml or lower.

An antibody according to the invention preferably does not inhibit chemokine binding in a binding assay to CCR1, CCR2, CCR3, CCR4, CCR6 and CXCR4 in an antibody concentration up to 100 µg/ml.

An antibody according to the invention preferably does not stimulate intracellular $Ca^{2+}$ increase, detected in CHO cells expressing CCR5 and Gα16 in an antibody concentration up to 50 µg/ml.

The antibody according to the invention is preferably of human isotype IgG1, IgG2, IgG3 or IgG4, whereby IgG1 or IgG4 are preferred.

The antibody according to the invention is preferably of IgG4 isotype, preferably with additional mutation S228P or is preferably of IgG1 isotype, modified in the hinge region at about aa220-240 between CH1 and CH2 (S. Angal et al., *Mol. Immunol.* (1993) 30:105-08) and/or the second inter-domain region of about aa 330 between CH2 and CH3 (numbering according to Kabat, (see e.g. G. Johnson and T. T. Wu, supra). Such modification avoids effector function (ADCC and/or CDC). Switching of IgG class can be performed by exchange of the constant heavy and light chains of the antibody by heavy and light chains from an antibody of the desired class, like IgG1 mutants or IgG4. Such methods are known in the state of the art.

The antibody according to the invention is preferably characterized by being of human subclass IgG1, containing at least one mutation in L234 (leucine at amino acid position 234), L235, D270, N297, E318, K320, K322, P331 and/or P329 (numbering according to EU index). Preferably the antibody is of human IgG1 type comprising mutations L234A (alanine instead of leucine at amino acid position 234) and L235A.

The invention relates therefore preferably to antibodies characterized in that said antibodies bind CCR5, contains a Fc part from human origin and do not bind human complement factor C1q and/or activates C3. Preferably the antibodies do not bind to at least one human Fcγ receptor.

The invention further provides hybridoma cell lines which produce monoclonal antibodies according to the invention. Preferred hybridoma cell lines according to the invention were deposited with Deutsche Sammlung von Mikroorganismen und Zellkulturen GmbH (DSMZ), Germany. The antibodies obtainable from said cell lines are presently preferred embodiments of the invention.

A further embodiment of the invention is an antibody binding to CCR5, characterized in that it is produced by cell line m<CCR5>Pz01.F3, m<CCR5>Pz04.1F6, m<CCR5>Pz03.1C5 or m<CCR5>Pz02.1C11. The sequence of the polynucleotides contained in this deposited materials, as well as the amino acid sequence of the polypeptides encoded thereby, are controlling in the event of any conflict with the sequences described in the sequence protocol.

The antibody according to the invention binds to human CCR5 in competition to an antibody from a cell line selected from the group consisting of antibodies A to E.

The invention further comprises a nucleic acid molecule encoding an antibody chain, a variable chain or a CDR domain thereof according to the invention. Encoded polypeptides are capable of assembling together with a respective other antibody chain to result in an antibody molecule against CCR5 according to the invention.

The invention further provides expression vectors containing said nucleic acids, and host cells containing such vectors for the recombinant production of such an antibody capable of expressing said nucleic acid in a prokaryotic or eukaryotic host cell.

Another aspect of the invention comprises a prokaryotic or eukaryotic host cell comprising a vector according to the invention.

Another aspect of the invention comprises a method for the production of a recombinant human antibody according to the invention, characterized by expressing a nucleic acid according to the invention in a prokaryotic or eukaryotic host cell and recovering said antibody from said cell. The invention further comprises the antibody obtainable by such a recombinant method.

Antibodies according to the invention show benefits for patients in need of a CCR5 targeting therapy. The antibodies according to the invention have new and inventive properties causing a benefit for a patient suffering from such a disease, especially suffering from immunosuppression, especially suffering from HIV infection.

Another aspect of the invention comprises a method for treating a patient suffering from immunosuppression, especially suffering from HIV infection, comprising administering to a patient diagnosed as having such disease (and therefore being in need of an such a therapy) an effective amount of an antibody binding to CCR5 according to the invention. The antibody is administered preferably in a pharmaceutical composition.

Another aspect of the invention comprises the use of an antibody according to the invention for the treatment of a patient suffering from immunosuppression and for the manufacture of a pharmaceutical composition according to the invention. In addition, the invention comprises a method for the manufacture of a pharmaceutical composition according to the invention.

The invention further comprises a pharmaceutical composition containing an antibody according to the invention in a pharmaceutically effective amount, optionally together with a buffer and/or an adjuvant useful for the formulation of antibodies for pharmaceutical purposes.

The invention further provides pharmaceutical compositions comprising such antibodies in a pharmaceutically acceptable carrier. In one embodiment, the pharmaceutical composition may be included in an article of manufacture or kit.

DETAILED DESCRIPTION OF THE INVENTION

All publications cited in this disclosure are incorporated herein by reference in their entirety.

Unless otherwise stated, the following terms used in this Application, including the specification and claims, have the definitions given below. As used in the specification and the appended claims, the singular forms "a", "an," and "the" include plural referents unless the context clearly dictates otherwise.

The term "antibody" encompasses the various forms of antibody structures including but not being limited to whole antibodies, antibody fragments. The antibody according to the invention is preferably a humanized antibody, chimeric antibody or further genetically engineered antibody as long as the characteristic properties according to the invention are retained.

"Antibody fragments" comprise a portion of a full length antibody, preferably the variable region thereof or at least the antigen binding portion thereof. Examples of antibody fragments include diabodies, single-chain antibody molecules, immunotoxins, and multi-specific antibodies formed from antibody fragments. In addition, antibody fragments comprise single chain polypeptides having the characteristics of a VH chain, namely being able to assemble together with a VL chain or of a VL chain binding to CCR5, namely being able to assemble together with a VH chain to a functional antigen binding pocket and thereby providing the property of inhibiting membrane fusion or HIV fusion with a target cell.

The terms "monoclonal antibody" or "monoclonal antibody composition" as used herein refer to a preparation of antibody molecules of a single amino acid composition. The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are especially preferred. Such mouse/human chimeric antibodies are the product of expressed immuno-globulin genes comprising DNA segments encoding mouse immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., S. L. Morrison et al., *Proc. Natl. Acad Sci. USA* (1984) 81:6851-6855; U.S. Pat. No. 5,202,238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a presently preferred embodiment, a mouse CDR is grafted into the framework region of a human antibody to prepare the "humanized antibody." See, e.g., L. Riechmann et al., *Nature* (1988) 332:323-27; and M. S. Neuberger et al., *Nature* (1985) 314:268-70. Particularly preferred CDRs correspond to those representing sequences recognizing the antigens noted above for chimeric and bifunctional antibodies.

The term "binding to CCR5" as used herein means binding of the antibody to CCR5 in a cell based in vitro ELISA assay (CCR5 expressing CHO cells). Binding is found if the antibody causes a S/N (signal/noise) ratio of 5 or more, preferably 10 or more at an antibody concentration of 100 ng/ml.

An antibody according to the invention shows a binding to the same epitope of CCR5 as does an antibody selected from the group consisting of the antibodies A to E or are inhibited in binding to CCR5 due to steric hindrance of binding. Epitope binding is investigated by using alanine mutation according to the method described by W. C. Olson et al., *J. Virol.* (1999) 73:4145-55 for epitope mapping. A signal reduction of 75% or more shows that the mutated amino acid(s) contribute to the epitope of said antibody. Binding to the same epitope is found, if the amino acids contributing to the epitope of the investigated antibody and the amino acids contributing to the epitope of antibody A, B, C, D or E are identical.

Antibody C, which shows lower $IC_{50}$ values than antibody 2D7 in HIV assays binds to an epitope including amino acids on the ECL2 domain of CCR5 (B. Lee et al., *J. Biol. Chem.* (1999) 274:9617-26) which is different from the epitope recognized by antibody 2D7 (2D7 binds to amino acids K171 and E172 of ECL2A but not to ECL2B amino acids 184-189). Epitope binding for antibody C is found to be 20% for CCR5 mutant K171A or E172A (if glu 172 is mutated to ala). 100% epitope binding is defined for wild-type CCR5. A further embodiment of the invention is therefore an antibody binding to CCR5 to the same epitope as antibody C binds.

The term "seven transmembrane chemokine molecular structure" as used herein refers to the natural structure, CCR5 shows when it is positioned in the cell membrane bilayer (see e.g. M. Oppermann, *Cell. Sig.* (2004) 16:1201-10). Like other 1b G protein-coupled receptors, CCR5 is composed of an extracellular N-terminal domain, a transmembrane domain and a cytoplasmatic C-terminal domain. The transmembrane domain consists of seven hydrophobic transmembrane segments, linked by three cytoplasmatic and three extracellular segments. The antibody according to the invention binds to CCR5 in its seven transmembrane chemokine molecular structure.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. Preferably an antibody according to the invention binds specifically to native but not to denatured CCR5. Such an antibody comprises preferably heavy chain CDR3 SEQ ID NO:17, and preferably in addition heavy chain CDRs SEQ ID NO:10, 11, 12, 14 and/or 15. Preferably such an antibody is antibody B, C, D or E, or comprises the variable regions of antibody B, C, D or E. Preferably an antibody binding to denatured CCR5 is antibody A or comprises the variable regions of antibody A.

The term "membrane fusion" refers to fusion between a first cell coexpressing CCR5 and CD4 polypeptides and a second cell expressing an HIV env protein. Membrane fusion is determined by luciferase reporter gene assay.

The term "inhibiting HIV fusion with a target cell" refers to inhibiting HIV fusion with a target cell measured in an assay comprising contacting the virus, in the presence of said target cell, with the antibody in a concentration effective to inhibit membrane fusion between the virus and said cell and measuring luciferase reporter gene activity.

The term "nucleic acid molecule", as used herein, is intended to include DNA molecules and RNA molecules. A nucleic acid molecule may be single-stranded or double-stranded, but preferably is double-stranded DNA.

The "variable region" (variable region of a light chain (VL), variable region of a heavy chain (VH)) as used herein denotes each of the pair of light and heavy chains which is involved directly in binding the antibody to the antigen. The domains of variable light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy variable chains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody and the antibody according to the invention is characterized by comprising in its heavy chain variable region the CDR3 sequence SEQ ID NO:16 or SEQ ID NO:17. CDR and FR regions are determined according to the standard definition of Kabat et al., Sequences of Proteins of Immunological Interest, 5th ed., Public Health Service, National Institutes of Health, Bethesda, Md. (1991)) and/or those residues from a "hypervariable loop".

The terms "nucleic acid" or "nucleic acid molecule", as used herein, are intended to include DNA molecules and RNA molecules. A nucleic acid molecule may be single-stranded or double-stranded, but preferably is double-stranded DNA.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are colinear, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

The "constant domains" are not involved directly in binding an antibody to an antigen, but exhibit various effector functions. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1 and IgA2. The heavy chain constant regions that correspond to the different classes of immunoglobulins are called α, δ, ε, γ, and μ, respectively. The antibodies according to the invention are preferably of IgG type.

As used herein the term "Fc part derived from human origin" denotes a Fc part which is either a Fc part of a human antibody of the subclass IgG4 or a Fc part of a human antibody of the subclass IgG1, IgG2 or IgG3 which is modified in such a way that no FcR (FcγRIIIa) binding and/or no C1q binding as defined below can be detected. A "Fc part of an antibody" is a term well known to the skilled artisan and defined on the basis of papain cleavage of antibodies. The antibodies according to the invention contain as Fc part a Fc part derived from human origin and preferably all other parts of the human constant regions. Preferably the Fc part is a human Fc part and especially preferred either from human IgG4 subclass or a mutated Fc part from human IgG1 subclass. Most preferred are the Fc parts and heavy chain constant regions shown in SEQ ID NO: 26 and 27, SEQ ID NO: 26 with mutations L234A and L235A or SEQ ID NO:27 with mutation S228P.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; and/or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

While IgG4 shows reduced Fc receptor (FcγRIIIa) binding, antibodies of other IgG subclasses show strong binding. However Pro238, Asp265, Asp270, Asn297 (loss of Fc carbohydrate), Pro329 and 234, 235, 236 and 237 Ile253, Ser254, Lys288, Thr307, Gln311, Asn434, and His435 are residues which provides if altered also reduced FcR binding (R. L. Shields et al., *J. Biol. Chem.* (2001) 276:6591-604; J. Lund et al., *FASEB J.* (1995) 9:115-19; A. Morgan et al., *Immunol* (1995) 86:319-24; and EP 0307434). Preferably an antibody according to the invention is in regard to FcR binding of IgG4 subclass or of IgG1 or IgG2 subclass with a mutation in S228, L234, L235 and/or D265, and/ or contains the PVA236 mutation. Presently preferred are the mutations S228P, L234A, L235A, L235E and/or PVA236. Especially preferred are mutations of IgG4 on S228P and IgG1 on L234A+L235A.

The Fc part of an antibody is directly involved in complement activation and C1q binding. While the influence of an antibody on the complement system is dependent on certain conditions, binding to C1q is caused by defined binding sites in the Fc part. Such binding sites are known in the state of the art and described e.g. by T. J. Lukas et al., *J. Immunol*. (1981) 127:2555-60; R. Brunhouse and J. J. Cebra, *Mol. Immunol.* (1979) 16:907-17; D. R. Burton et al., *Nature* (1980) 288: 338-44; J. E. Thommesen et al., *Mol. Immunol.* (2000) 37:995-1004; E. E. Idusogie et al., *J. Immunol.* (2000) 164: 4178-84; M. Hezareh et al., *J. Virol*. (2001) 75:12161-68; A. Morgan et al., supra; and EP 0307434. Such binding sites are e.g. L234, L235, D270, N297, E318, K320, K322, P331 and P329 (numbering according to EU index of Kabat). Antibodies of subclass IgG1, IgG2 and IgG3 usually show complement activation and C1q and C3 binding, whereas IgG4 do not activate the complement system and do not bind C1q and C3.

The present invention refers to an antibody that specifically binds CCR5 and does not bind Fc receptor and/ or complement factor C1q. The antibody does not elicit antibody-dependent cellular cytotoxicity (ADCC) and/or complement dependent cytotoxicity (CDC). Preferably, this antibody is characterized in that it binds CCR5, contains a Fc part derived from human origin and does not bind Fc receptor and/or complement factor C1q. More preferably, this antibody is a human or humanized antibody or a T-cell antigen depleted antibody e.g. according to WO 98/52976 and WO 00/34317. C1q binding can be measured according to E. E. Idusogie et al., supra. No "C1q binding" is found if OD 492-405 nm is lower than 15% of the value for human C1q binding for the antibody with unmodified (wild-type) Fc part at an antibody concentration of 8 μg/ml. ADCC can be measured as binding of the antibody to human FcγRIIIa on human NK cells. Binding is determined at an antibody concentration of 20 μg/ml. "No FcR binding or no ADCC" means a binding of up to 30% to human FcγRIIIa on human NK cells at an antibody concentration of 20 μg/ml compared to the binding of the same antibody as human IgG1 (SEQ ID NO:26).

The antibodies according to the invention include, in addition, such antibodies having "conservative sequence modifications" (variant antibodies), nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CCR5 antibody can be preferably replaced with another amino acid residue from the same side chain family. A "variant" anti-CCR5 antibody, refers therefore herein to a molecule which differs in amino acid sequence from a "parent"

anti-CCR5 antibody amino acid sequence by up to ten, preferably from about two to about five, additions, deletions and/or substitutions in one or more variable region of the parent antibody outside heavy chain CDR3. Each other CDR region comprises at maximum one single amino addition, deletion and/or substitution. The invention comprises a method of modifying the CDR amino acid sequence of an parent antibody binding to CCR5, characterized in selecting a heavy chain CDR selected from the group consisting of SEQ ID NOs: 1, 3, 5 and 7 and/or an antibody light chain CDR selected from the group consisting of SEQ ID NOs: 2, 4, 6 and 8, providing a nucleic acid encoding said initial amino acid CDR sequence, modifying said nucleic acid in that one amino acid is modified in heavy chain CDR1, one amino acid is modified in heavy chain CDR2, 1-3 amino acid are modified in light chain CDR1, 1-3 amino acids are modified in light chain CDR2, and/or 1-3 amino acids are modified in light chain CDR3, expressing said modified CDR amino acid sequence in an antibody structure, measuring whether said antibody binds to CCR5 and selecting said modified CDR if the antibody binds to CCR5. Preferably such modifications are conservative sequence modifications.

Amino acid substitutions can be performed by mutagenesis based upon molecular modeling as described by L. Riechmann et al., *Nature* (1988) 332:323-27 and C. Queen et al., *Proc. Natl. Acad. Sci. USA* (1989) 86:10029-33.

A further embodiment of the invention is a method for the production of an antibody against CCR5 which do not bind Fcγ receptor and/or C1q characterized in that the sequence of a nucleic acid encoding the heavy chain of an human IgG1 type antibody binding to CCR5 is modified in such a manner that said modified antibody does not bind C1q and/or Fcγ receptor, said modified nucleic acid and the nucleic acid encoding the light chain of said antibody are inserted into an expression vector, said vector is inserted in a eukaryotic host cell, the encoded protein is expressed and recovered from the host cell or the supernatant. Preferably the antibody is modified by "class switching", i.e. change or mutation of the Fc part (e.g. from IgG1 to IgG4 and/or IgG1/IgG4 mutation) preferably defined as IgG1v1 (PVA-236; GLPSS331 as specified by E233P; L234V; L235A; delta G236; A327G; A330S; P331S), IgG1v2 (L234A; L235A) and IgG4v1 (S228P; L235E) and IgG4x (S228P).

Identity or homology with respect to the sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind human CCR5 and preferably has properties, which are superior to those of the parent antibody. For example, the variant may have reduced side effects during treatment.

The "parent" antibody herein is one, which is encoded by an amino acid sequence used for the preparation of the variant. Preferably, the parent antibody has a human framework region and, if present, has human antibody constant region(s). For example, the parent antibody may be a humanized or human antibody.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for injection or infusion.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NS0 cells, SP2/0 cells, HEK293 cells, COS cells, yeast, or *E. coli* cells, and the antibody is recovered from the cells (supernatant or cells after lysis).

Recombinant production of antibodies is well-known in the state of the art and described, for example, in the review articles of S. C. Makrides, *Protein Expr. Purif.* (1999) 17:183-202; S. Geisse et al., *Protein Expr. Purif.* (1996) 8:271-82; R. J. Kaufman, *Mol. Biotechnol.* (2000) 16:151-61; R. G. Werner, *Drug Res.* (1998) 48:870-80.

The antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art. See F. Ausubel et al., ed. Current Protocols in Molecular Biology, Greene Publishing and Wiley Interscience, New York (1987).

Expression in NS0 cells is described by, e.g., L. M. Barnes et al., *Cytotechnology* (2000) 32:109-23; and L. M. Barnes et al., *Biotech. Bioeng.* (2001) 73:261-70. Transient expression is described by, e.g., Y. Durocher et al., *Nucl. Acids. Res.* (2002) 30:E9. Cloning of variable domains is described by R. Orlandi et al., *Proc. Natl. Acad. Sci. USA* (1989) 86:3833-37; P. Carter et al., *Proc. Natl. Acad. Sci. USA* (1992) 89:4285-89; and L. Norderhaug et al., *J. Immunol. Meth* (1997) 204:77-87. A presently preferred transient expression system (HEK 293) is described by E.-J. Schlaeger and K. Christensen in *Cytotechnology* (1999) 30:71-83 and by E.-J. Schlaeger, *J. Immunol. Methods* (1996) 194:191-99.

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants of human CCR5 antibody are prepared by introducing appropriate nucleotide changes into the antibody DNA, or by peptide synthesis. Such modifications can be performed, however, only in a very limited range, e.g. as described above. For example, the modifications do not alter the abovementioned antibody characteristics such as the IgG isotype and epitope binding, but may improve the yield of the recombinant production, protein stability or facilitate the purification.

Any cysteine residue not involved in maintaining the proper conformation of the anti-CCR5 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically N-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Nucleic acid molecules encoding amino acid sequence variants of anti-CCR5 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-CCR5 antibody.

Another type of covalent modification involves chemically or enzymatically coupling glycosides to the antibody. These procedures are advantageous in that they do not require production of the antibody in a host cell that is capable of N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in J. D. Aplin and J. C. Wriston, Jr., *CRC Crit. Rev. Biochem.* (1981) 4:259-306.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by H. T. Sojahr and O. P. Bahl, *Arch. Biochem. Biophys.* (1987) 259:52-57 and by A. S. Edge et al., *Anal. Biochem.* (1981) 118:131-37. Enzymatic cleavage of carbohydrate moieties on antibodies can be achieved by the use of a variety of endo- and exo-glycosidases as described by N. R. Thotakura and O. P. Bahl, *Meth. Enzymol.* (1987) 138:350-59.

Another type of covalent modification of the antibody comprises linking the antibody to any of a variety of nonproteinaceous polymers, for example polyethylene glycol, polypropylene glycol, and/or polyoxyalkylenes, for example as set forth in U.S. Pat. Nos. 4,640,835; 4,496,689; 4,301,144; 4,670,417; 4,791,192 or 4,179,337.

The reconstructed heavy and light chain variable regions are combined with sequences of promoter, translation initiation, constant region, 3' untranslated, polyadenylation, and transcription termination to form expression vector constructs. The heavy and light chain expression constructs can be combined into a single vector, co-transfected, serially transfected, or separately transfected into host cells which are then fused to form a single host cell expressing both chains.

The invention further comprises the use of an antibody according to the invention for the diagnosis of AIDS susceptibility in vitro, preferably by an immunological assay determining the binding between soluble CCR5 of a human plasma sample (T. Tsimanis, *Immunol Lett* (2005) 96:55-61) and the antibody according to the invention. Expression of CCR5 has a correlation with disease progression, and can be used to identify low or high risk individuals for AIDS susceptibility. For diagnostic purposes, the antibodies or antigen binding fragments can be labeled or unlabeled. Typically, diagnostic assays entail detecting the formation of a complex resulting from the binding of an antibody or fragment to CCR5.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The invention comprises the use of the antibodies according to the invention for the treatment of a patient suffering from immunosuppression, such as immunosuppression in a patient with immunodeficiency syndromes such as AIDS, in a patient undergoing radiation therapy, chemotherapy, therapy for autoimmune disease or other drug therapy (e.g., corticosteroid therapy), which causes immunosuppression, GvHD or HvGD (e.g. after transplantation). The invention comprises also a method for the treatment of a patient suffering from such immunosuppression.

The invention further provides a method for the manufacture of a pharmaceutical composition comprising an effective amount of an antibody according to the invention together with a pharmaceutically acceptable carrier and the use of the antibody according to the invention for such a method.

The invention further provides the use of an antibody according to the invention in an effective amount for the manufacture of a pharmaceutical agent, preferably together with a pharmaceutically acceptable carrier, for the treatment of a patient suffering from immunosuppression.

ANTIBODY DEPOSIT

| Cell line | Deposition No. | Date of Deposit |
|---|---|---|
| m<CCR5>Pz01.F3 | DSM ACC 2681 | 18 Aug. 2004 |
| m<CCR5>Pz02.1C11 | DSM ACC 2682 | 18 Aug. 2004 |
| m<CCR5>Pz03.1C5 | DSM ACC 2683 | 18 Aug. 2004 |
| m<CCR5>Pz04.1F6 | DSM ACC 2684 | 18 Aug. 2004 |

DESCRIPTION OF THE SEQUENCES

| | |
|---|---|
| SEQ ID NO: 1 | <CCR5>Pz01.F3 heavy chain, variable domain |
| SEQ ID NO: 2 | <CCR5>Pz01.F3 light chain, variable domain |
| SEQ ID NO: 3 | <CCR5>Pz02.1C11 heavy chain, variable domain |
| SEQ ID NO: 4 | <CCR5>Pz02.1C11 light chain, variable domain |
| SEQ ID NO: 5 | <CCR5>Pz03.1C5 heavy chain, variable domain |
| SEQ ID NO: 6 | <CCR5>Pz03.1C5 light chain, variable domain |
| SEQ ID NO: 7 | <CCR5>F3.1H12.2E5 heavy chain, variable domain |
| SEQ ID NO: 8 | <CCR5>F3.1H12.2E5 light chain, variable domain |
| SEQ ID NO: 9 | Heavy chain CDR1 |
| SEQ ID NO: 10 | Heavy chain CDR1 |
| SEQ ID NO: 11 | Heavy chain CDR1 |
| SEQ ID NO: 12 | Heavy chain CDR1 |
| SEQ ID NO: 13 | Heavy chain CDR2 |
| SEQ ID NO: 14 | Heavy chain CDR2 |
| SEQ ID NO: 15 | Heavy chain CDR2 |
| SEQ ID NO: 16 | Heavy chain CDR3 |
| SEQ ID NO: 17 | Heavy chain CDR3 |
| SEQ ID NO: 18 | Light chain CDR1 |
| SEQ ID NO: 19 | Light chain CDR1 |
| SEQ ID NO: 20 | Light chain CDR1 |
| SEQ ID NO: 21 | Light chain CDR2 |
| SEQ ID NO: 22 | Light chain CDR2 |
| SEQ ID NO: 23 | Light chain CDR2 |
| SEQ ID NO: 24 | Light chain CDR3 |
| SEQ ID NO: 25 | Light chain CDR3 |
| SEQ ID NO: 26 | γ1 heavy chain constant region |
| SEQ ID NO: 27 | γ4 heavy chain constant region |
| SEQ ID NO: 28 | κ light chain constant region |

ANTIBODY NOMENCLATURE

| | | |
|---|---|---|
| <CCR5>Pz01.F3: | Antibody A | SEQ ID NO: 1, 2 |
| <CCR5>Pz02.1C11: | Antibody B | SEQ ID NO: 3, 4 |
| <CCR5>Pz03.1C5: | Antibody C | SEQ ID NO: 5, 6 |
| <CCR5>F3.1H12.2E5: | Antibody D | SEQ ID NO: 7, 8 |
| <CCR5>Pz04.1F6: | Antibody E | |

The following examples, references and sequence listing are provided to aid the understanding of the present invention, the true scope of which is set forth in the appended claims. It is understood that modifications can be made in the procedures set forth without departing from the spirit of the invention.

EXAMPLES

Example 1

Production of Monoclonal Antibodies to Human CCR5

A) Immunization of Mice: Female BALB/C mice are given a primary intraperitoneal immunization with $10^7$ CCR5 expressing cells (CHO or L1.2) together with complete Freund's adjuvant (CFA). This is followed by one further intraperitoneal immunization after 4-6 weeks with again the same $10^7$ CCR5 expressing cells in incomplete Freund's adjuvant (IFA). Thereafter each mouse is administered with again $10^7$ CCR5 expressing cells (CHO or L1.2) in PBS at 4-6 weeks intervals. Subsequently, the last immunizations are carried out ip with again 1 CCR5 expressing cells or intravenously using $2\times10^6$ CCR5-expressing cells on the 3rd or 4th day before fusion.

B) Fusion and Cloning: The spleen cells of the mice immunized according to a) are fused with myeloma cells according to Galfré, Meth Enzymol (1981) 73:3. About $1\times10^8$ spleen cells of the immunized mouse are mixed with about the same number of myeloma cells (P3X63-Ag8-653, ATCC CRL 1580), fused and cultivated subsequently in HAZ medium (100 mmol/l hypoxanthine, 1 µg/ml azaserine in RPMI 1640+ 10% FCS). After about 10 days the primary cultures are tested for specific antibody production. Primary cultures which exhibit a positive reaction with CCR5in cell ELISA and no cross-reaction with non-transfected parental cells, are cloned in 96-well cell culture plates by means of limiting dilution or a fluorescence activated cell sorter. The cell lines deposited were obtained in this manner.

C) Recombinant Production of Antibodies: Vectors for expression of a chimeric antibody, consisting of human constant regions linked to murine variable regions, can been constructed as follows. Two chimeric heavy chain expression vectors are constructed consisting of the anti-CCR5 mouse VH linked to human IgG1 and human IgG4 constant regions in the expression vector pSVgpt. A chimeric light chain vector is constructed consisting of anti-CCR5 mouse VK linked to human C Kappa in the expression vector pSVhyg. The 5'-flanking sequence including the leader signal peptide, leader intron and the murine immunoglobulin promoter, and 3 flanking sequence including the splice site and intron sequence is introduced using the vectors VH-PCR1 and VK-PCR1 as templates. The heavy and light chain expression vectors are co-transfected into NS0 cells (ECACC No 85110503, a non-immunoglobulin producing mouse myeloma). Transfected cell clones are screened for production of human antibody by ELISA for human IgG.

Example 2

Construction of Expression Plasmids for Mutant (Variant) Anti-CCR5 IgG1 and IgG4

Expression plasmids encoding mutant anti-CCR5 γ1- and γ4-heavy chains can be created by site-directed mutagenesis of the wild type expression plasmids using the QUICK-CHANGE™ Site-Directed mutagenesis Kit (Stratagene) and are described in table 1. Amino acids are numbered according to EU numbering (G. M. Edelman et al., Proc. Natl. Acad. Sci. USA (1969) 63:78-85; E. A. Kabat et al., Sequences of Proteins of Immunological Interest, Fifth Ed., NIH Publication No. 91-3242 (1991)).

TABLE 1

| Isotype | Abbreviation | Mutations* | Description |
|---|---|---|---|
| IgG1 | IgG1v1 | PVA-236; GLPSS331 as specified by E233P; L234V; L235A; delta | The amino acid sequence $Glu_{233}Leu_{234}-Leu_{235}Gly_{236}$ of the human γ1-heavy chain (SEQ ID NO:26, amino acids 116-119) is replaced by the amino acid sequence $Pro_{233}Val_{234}Ala_{235}$ of the human γ2-heavy chain. The amino acid |

TABLE 1-continued

| Isotype | Abbreviation | Mutations* | Description |
|---|---|---|---|
| | | G236; A327G; A330S; P331S | sequence $Ala_{327}Leu_{328}Pro_{329}Ala_{330}Pro_{331}$ of the human γ1-heavy chain is (SEQ ID NO:26, amino acids 210-214) replaced by the amino acid sequence $Gly_{327}Leu_{328}Pro_{329}Ser_{330}Ser_{331}$ (SEQ ID NO:27, amino acids 207-212) of the human γ4-heavy chain |
| IgG1 | IgG1v2 | L234A; L235A | The amino acid sequence $Leu_{234}Leu_{235}$ of the human Y1-heavy chain is replaced by the amino acid sequence $Ala_{234}Ala_{235}$ |
| IgG4 | IgG4v1 | S228P; L235E | $Ser_{228}$ of the human Y4-heavy chain is replaced by $Pro_{228}$ and $Leu_{235}$ of the human Y4-heavy chain is replaced by $Glu_{235}$ |
| IgG4 | IgG4x | S228P | $Ser_{228}$ of the human Y4-heavy chain is replaced by $Pro_{228}$ |

*Explanation of mutations: S228P means that serine at Kabat amino acid position 228 is changed to proline.

Example 3

Cell-Cell Fusion Assay

At day 1, gp160-expressing HeLa cells ($2 \times 10^4$ cells/50 µl/well) are seeded in a white 96 microtiter plate in DMEM medium supplemented with 10% FCS and 2 µg/ml doxycycline. At day 2, 100 µl of supernatant sample or antibody control per well is added in a clear 96 microtiter plate. Then 100 µl containing $8 \times 10^4$ CEM-NKr-Luc suspension cells in medium are added and incubated 30 min at 37° C. The Hela cell culture medium is aspirated from the 96 well plate, 100 µl from the 200 µl antibody/CEM-NKr-Luc mixture is added and incubated over night at 37° C. At day 3, 100 µl/well BRIGHT-GLO™ Luciferase assay substrate (1,4-dithiothreitol and sodium dithionite; Promega Corp. USA) is added and luminescence is measured after a minimum of 15 min incubation at RT Materials:

Hela-R5-16 cells (cell line to express HIV gp160 upon doxycycline induction) are cultured in DMEM medium containing nutrients and 10% FCS with 400 µg/ml G418 and 200 µg/ml Hygromycin B.

CEM.NKR-CCR5-Luc (Catalog Number: 5198) is a T-cell line available from NIH AIDS Research & Reference Reagent Program McKesson BioServices Corporation Germantown, Md. 20874, USA. Cell Type: CEM.NKR-CCR5 (Cat. #4376) was transfected (electroporation) to express the luciferase gene under the transcriptional control of the HIV-2 LTR and propagated in RPMI 1640 containing 10% fetal bovine serum, 4 mM glutamine, penicillin/streptomycin and 0.8 mg/ml geneticin sulfate (G418). Growth Characteristics: Round lymphoid cells, morphology not very variable. Cells grow in suspension as single cells, which can form small clumps. Split 1:10 twice weekly. Special Characteristics: Express luciferase activity after transactivation of the HIV-2 LTR. Suitable for infection with primary HIV isolates, for neutralization and drug-sensitivity assays (C. Spenlehauer et al., *Virology* (2001) 280:292-300; A. Trkola et al., *J. Virol.* (1999) 73:8966-74). The cell line was obtained through the NIH AIDS Research and Reference Reagent Program, NIAID, NIH from Drs. John Moore and Catherine Spenlehauer.

BRIGHT-GLO™ Luciferase assay buffer (Promega Corp. USA, Part No E2264B)

BRIGHT-GLO™ Luciferase assay substrate (Promega Corp. USA, part No EE26B)

Results:

$IC_{50}$ values are 0.38 µg/ml for antibody C, 0.79 µg/ml for antibody B, and 7.0 µg/ml for antibody A. $IC_{50}$ values are e.g. also measured in the PHENOSENSE™ HIV assay (ViroLogic, Inc. USA) using JRCSF strain. The $IC_{50}$ values are 0.16 µg/ml for antibody C, 0.17 µg/ml for antibody B, 0.82 µg/ml for antibody A and 1.4 µg/ml for antibody 2D7.

Example 4

Antiviral Assay with Live Virus

PBMCs are prepared from buffy coat isolated by density-gradient centrifugation using LYMPHOPREP™ (Nycomed Pharma AG, Oslo, Norway). Cells from four different donors were mixed, stimulated for 1 day with PHA and subsequently cultured in RPMI medium containing 1% penicillin/streptomycin, 1% glutamax, 1% sodium pyruvate, 1% non-essential amino acids and 10% FBS, for two days in the presence of 5 U/ml IL-2.

100,000 PBMC in 50 µl are added to 100 µl of an antibody solution (serial dilution ranged between 0.006-17.5 µg/ml, in supplemented RPMI medium and infected with 250 $TCID_{50}$ of NLBal (NL4.3 strain (A. Adachi et al., *J. Virol.* (1986) 59:284-91) with the env of BaL (gp120)) or alternatively JRCSF (O'Brien, W. A., et al., Nature 348 (1990) 69-73) in a volume of 50 µl. The mixture is incubated for 6 days at 37° C. in $CO_2$ incubator. The supernatant was harvested and subsequently diluted 1:50 with 5U/ml IL-2 supplemented RPMI medium.

Measurement of p24 is performed by a HIV-24 ELISA (Perkin-Elmer, USA). The samples are then neutralized and transferred to microplate wells which are coated with a highly specific mouse monoclonal antibody to HIV-1 p24. The immobilized monoclonal antibody captures HIV-1 p24. Cell culture samples do not require disruption and are added directly to the monoclonal antibody-coated microplate wells. The captured antigen is complexed with biotinylated polyclonal antibody to HIV-1 p24, followed by a streptavidin-HRP (horseradish peroxidase) conjugate. The resulting complex is detected by incubation with ortho-phenylenediamine-HCl (OPD) which produces a yellow color that is directly proportional to the amount of HIV-1 p24 captured. The absorbance of each microplate well is determined using a microplate reader and calibrated against the absorbance of an HIV-1 p24 antigen standard or standard curve. The results are shown in table 2.

TABLE 2

Inhibition of HIV growth in human PBMC

| | IC50 [µg/ml] | |
|---|---|---|
| Antibody | JRCSF | NI-Bal |
| 2D7 | 0.271 | 0.076 |
| A | 0.016 | 0.045 |
| B | 0.025 | 0.025 |
| C | 0.013 | 0.029 |

Example 5

CCR5 Cell ELISA 20,000 CHO cells recombinantly expressing CCR5 are seeded per 96 well plate, and incubated overnight at 37° C. Thereafter medium is aspirated and 40 µl fresh medium is added. 10 µl in medium-diluted antibody is added and incubated 2 hours at 4° C. Medium is aspirated, 100 µl glutardialdehyde (c=0.05% in PBS) is added and incubated 10 min at room temperature. After washing 3× with 200 µl PBS, 50 µl detection antibody 1 (1,000 diluted in ELISA blocking) is added and incubated 2 hours at room temperature. 50 µl 3,3',5,5'-Tetramethylbenzidine (TMB) is added and the reaction stopped after 7 min. Optical Density is measured at 450 nm (versus 620 nm).

First antibody: Pharmingen 2D7 (CD 195; Cat. Nr. 555990) or antibody B/C.

Second antibody: Detection antibody (conjugate of antibody against murine IgG and POD; Biorad, #170-6516, 1:1000 diluted).

Medium: HAM's F-12 or GIBCO with Glutamax, 10% FCS, 200 µg/ml Hygromycin (Roche Diagnostics GmbH, DE).

ELISA-Blocking: Roche Diagnostics GmbH, DE #1112589, 10% (v/v) solution in water, 1/10 diluted in PBS.

TMB: Roche Diagnostics GmbH, DE #1432559, solution for use.

Example 6

Potential of CCR5 Mabs to Bind to FcγRIIIa on NK Cells

To determine the ability of the antibodies of the invention to bind to FcγRIIIa (CD16) on Natural Killer (NK) cells, Peripheral Blood Mononuclear Cells (PBMCs) are isolated and incubated with 20 µg/ml of antibody and control antibodies in the presence or absence of 20 µg/ml of a blocking mouse antibody to FcγRIIIa (anti-CD16, clone 3G8, RDI, Flanders, N.J.), to verify binding via FcγRIIIa. As negative controls, human IgG2 and IgG4 (The Binding Site), that do not bind FcγRIIIa, are used. Human IgG1 and IgG3 (The Binding Site) are included as positive controls for FcγRIIIa binding. Bound antibodies on NK cells are detected by FACS analysis using a PE-labeled mouse anti-human CD56 (NK-cell surface marker) antibody (BD Biosciences Pharmingen, San Diego, Calif.) in combination with a FITC-labeled goat F(ab)$_2$ anti-human IgG (Fc) antibody (Protos Immunoresearch, Burlingame, Calif.). Maximum binding (Bmax) is determined at an antibody concentration of 20 µg/ml. Control antibody (human IgG4) shows up to 30% $B_{max}$ compared to 100% $B_{max}$ for human IgG1. Therefore "no FcγRIIIa binding or no ADCC" means at an antibody concentration of 20 µg/ml a $B_{max}$ value of up to 30% compared to human IgG1.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

LIST OF REFERENCES

A. Adachi et al., *J. Virol.* (1986) 59:284-91
S. Angal et al., *Mol. Immunol.* (1993) 30:105-08
J. D. Aplin and J. C. Wriston, Jr., *CRC Crit. Rev. Biochem.* (1981) 4:259-306
F. Ausubel et al., ed. Current Protocols in Molecular Biology, Greene Publishing and Wiley Interscience, New York (1987)
L. M. Barnes et al., *Biotech. Bioeng.* (2001) 73:261-270
L. M. Barnes et al., *Cytotechnology* (2000) 32:109-123
E. A. Berger, *AIDS* (1997) 11 (Suppl. A):S3-S16
P. D. Bieniasz and b. R. Cullen, *Frontiers in Bioscience* (1998) 3:44-58
R. Brunhouse and J. J. Cebra, *Mol. Immunol.* (1979) 16:907-17
D. R. Burton et al., *Nature* (1980) 288:338-44
P. Carter et al., *Proc. Natl. Acad. Sci. USA* (1992) 89:4285-89
F. Cocchi et al., *Science* (1995) 270:1811-15
M. Dean et al., *Science* (1996) 273:1856-62
Y. Durocher et al., *Nucl. Acids. Res.* (2002) 30:E9
G. M. Edelman et al., *Proc. Natl. Acad. Sci. USA* (1969) 63:78-85
A. S. Edge et al., *Anal. Biochem.* (1981) 118:131-37
EP 1 144 006
EP 1 161 456
EP 1 207 202
EP 1 263 791
EP 1 322 332
EP 0 307 434
S. Geisse et al., *Protein Expr. Purif.* (1996) 8:271-82
M. Hezareh et al., *J. Virol.* (2001) 75:12161-68
E. E. Idusogie et al., *J. Immunol.* (2000) 164:4178-84
G. Johnson and T. T. Wu, *Nucleic Acids Res.* (2000) 28:214-218
Kabat et al., Sequences of Proteins of Immunological Interest, 5th ed., Public Health Service, National Institutes of Health, Bethesda, Md., NIH Publication No. 91-3242 (1991)
R. J. Kaufman, *Mol. Biotechnol.* (2000) 16:151-61
W. M. Kazmierski et al., *Curr. Drug Targets Infect. Disord.* (2002) 2:265-78
J. M. Kilby and J. J. Eron, *N. Engl. J. Med.* (2003) 348:2228-38
A. Lazzarin et al., *N. Engl J. Med.* (2003) 348:2186-95
B. Lee et al., *J. Biol. Chem.* (1999) 274:9617-26
T. Lehner, *Trends Immunol.* (2002) 23:347-51
D. R. Littman, *Cell* (1998) 93:677-80
T. J. Lukas et al., *J. Immunol.* (1981) 127:2555-60
J. Lund et al. *FASEB J.* (1995) 9:115-19
S. C. Makrides, *Protein Expr. Purif.* (1999) 17:183-202
A. Morgan et al., *Immunology* (1995) 86:319-24
S. L. Morrison et al., *Proc. Natl. Acad. Sci. USA* (1984) 81:6851-55
A. Mueller and P. G. Strange, *Int. J. Biochem. Cell Biol.* (2004) 36:35-38
M. S. Neuberger et al., *Nature* (1985) 314:268-70
L. Norderhaug et al., *J. Immunol. Meth* (1997) 204:77-87
W. A. O'Brien et al., *Nature* (1990) 348:69-73
W. C. Olson et al., *J. Virol.* (1999) 73:4145-55
M. Oppermann, *Cell. Sig.* (2004) 16:1201-10
R. Orlandi et al., *Proc. Natl. Acad. Sci. USA* (1989) 86:3833-37

T. C. Pierson and R. W. Doms, *Immuno. Lett.* (2003) 85:113-18
C. Queen et al., *Proc. Natl. Acad. Sci. USA* (1989) 86:10029-33
L. Riechmann et al., *Nature* (1988) 332:323-27
D. Rossi and A. Zlotnik, *Annu. Rev. Immunol.* (2000) 18:217-43
M. Samson et al., *J. Biol. Chem* (1997) 272:24934-41
M. Samson et al., *Nature* (1996) 382:722-25
E.-J. Schlaeger and K. Christensen, *Cytotechnology* (1999) 30:71-83
E.-J. Schlaeger, *J. Immunol. Methods* (1996) 194:191-99
D. Schols, *Curr. Top. Med. Chem.* (2004) 4:883-93
M. K. Schwarz and T. N. Wells, *Nat. Rev. Drug Discov.* (2002) 1:347-58
R. L. Shields et al. *J. Biol. Chem.* (2001) 276:6591-604
H. T. Sojahr and O. P. Bahl, *Arch. Biochem. Biophys.* (1987) 259:52-57
C. Spenlehauer et al., *Virology* (2001) 280:292-300
J. E. Thommesen et al., *Mol. Immunol.* (2000) 37:995-1004
N. R. Thotakura and O. P. Bahl, *Meth. Enzymol.* (1987) 138:350-59
A. Trkola et al., *J. Virol.* (1999) 73:8966-74
T. Tsimanis, *Immunology Letters* (2005) 96:55-61
R. G. Werner, *Drug Res.* (1998) 48:870-80
U.S. Pat. No. 4,179,337
U.S. Pat. No. 4,301,144
U.S. Pat. No. 4,496,689
U.S. Pat. No. 4,640,835
U.S. Pat. No. 4,670,417
U.S. Pat. No. 4,791,192
U.S. Pat. No. 5,202,238
U.S. Pat. No. 5,204,244
U.S. Pat. No. 6,528,625
U.S. Pat. No. 6,610,834
US 2001/0000241
US 2002/0048786
US 2002/0061834
US 2002/0106374
US 2002/0146415
US 2002/0147147
US 2003/0003440
US 2003/0044411
US 2003/0049251
US 2003/0099645
US 2003/0100058
US 2003/0152913
US 2003/0165988
US 2003/0166024
US 2003/0166870
US 2003/0195348
US 2003/0228306
US 2004/0043033
WO 87/05330
WO 98/52976
WO 00/34317
WO 01/42308
WO 01/43779
WO 01/58915
WO 01/58916
WO 02/22077
WO 02/083172
WO 03/033666
WO 03/066830
WO 03/072766

---

What is claimed:

1. An antibody that binds to CCR5, comprising variable heavy and light regions independently selected from the group consisting of
   a) the heavy chain (VH) variable domain of SEQ ID NO:1 and the light chain (VH) variable domain of SEQ ID NO:2;
   b) the heavy chain variable domain of SEQ ID NO:3 and the light chain variable domain of SEQ ID NO:4;
   c) the heavy chain variable domain of SEQ ID NO:5 and the light chain variable domain of SEQ ID NO:6;
   d) the heavy chain variable domain of SEQ ID NO:7 and the light chain variable domain of SEQ ID NO:8; and
   e) a CCR5-binding fragment of any of a)-d).

2. The antibody of claim 1, wherein said antibody is the antibody produced by hybridoma cell lines m<CCR5>Pz01.F3, m<CCR5>Pz04.1F6, m<CCR5>Pz03.1C5 or m<CCR5>Pz02.1C11.

3. The antibody of claim 1, wherein said antibody is of IgG4 isotype or IgG1 isotype, by a modification selected from the group consisting of:

For an antibody of isotype IgG1, replacing the amino acids $Glu_{233}Leu_{234}Leu_{235}Gly_{236}$ of the heavy chain (SEQ ID NO:26, amino acids 116-119) with $Pro_{233}Val_{234}Ala_{235}$ and amino acids $Ala_{327}Leu_{328}Pro_{329}Ala_{330}Pro_{331}$ (SEQ ID NO:26, amino acids 210-214) with $Gly_{327}Leu_{328}Pro_{329}Ser_{330}Ser_{331}$ (SEQ ID NO:27, amino acids 207-212);

For an antibody of isotype IgG1, replacing the amino acids $Leu_{234}Leu_{235}$ of the heavy chain (SEQ ID NO:26, amino acids 117-118) with $Ala_{234}Ala_{235}$;

For an antibody of isotype IgG4, replacing $Ser_{228}$ of the heavy chain with $Pro_{228}$, and replacing $Leu_{235}$ of the heavy chain with $Glu_{235}$;

For an antibody of isotype IgG4, replacing $Ser_{228}$ of the heavy chain with $Pro_{228}$.

4. A hybridoma cell line selected from the group consisting of m<CCR5>Pz01.F3, m<CCR5>Pz04.1F6, m<CCR5>Pz03.1C5, and m<CCR5>Pz02.1C11.

5. A pharmaceutical composition comprising:
   an antibody according to claim 1 in a pharmaceutically effective amount, and
   a pharmaceutically acceptable excipient.

6. A pharmaceutical composition comprising:
   an antibody according to claim 3 in a pharmaceutically effective amount, and
   a pharmaceutically acceptable excipient.

7. A pharmaceutical composition comprising:
   an antibody according to claim 2 in a pharmaceutically effective amount, and
   a pharmaceutically acceptable excipient.

* * * * *

UNITED STATES PATENT AND TRADEMARK OFFICE
CERTIFICATE OF CORRECTION

PATENT NO. : 7,615,216 B2
APPLICATION NO. : 11/394439
DATED : November 10, 2009
INVENTOR(S) : Brandt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 145 days.

Signed and Sealed this

Nineteenth Day of October, 2010

David J. Kappos
*Director of the United States Patent and Trademark Office*